US00PP13065P2

(12) United States Plant Patent
Roelof Van Tol

(10) Patent No.: US PP13,065 P2
(45) Date of Patent: Oct. 8, 2002

(54) DELPHINIUM PLANT NAMED 'DARWIN'S PINK INDULGENCE'

(75) Inventor: Benjamin Roelof Van Tol, Abbenes (NL)

(73) Assignee: Witteman and Company Multiflora, Hillegom (NL)

( * ) Notice: Subject to any disclaimer, the term of this patent is extended or adjusted under 35 U.S.C. 154(b) by 0 days.

(21) Appl. No.: 09/714,468

(22) Filed: Nov. 16, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu

(57) ABSTRACT

The new variety of Delphinium, 'Darwin's Pink Indulgence' is characterized by its compact growth habit and by its purple violet, fully double flowers that are long blooming and long lasting as a cut flower.

4 Drawing Sheets

BACKGROUND OF THE INVENTION

The present invention relates to a new and distinct cultivar of Delphinium. Botanically, it belongs to the Genus Delphinium and is a hybrid belonging to the Elatum Group (also referred to as *Delphinium elatum* types). The new invention will be referred to hereafter by its cultivar name 'Darwin's Pink Indulgence'. Delphiniums are hardy perennials grown for landscape use.

The new Delphinium, 'Darwin's Pink Indulgence', was discovered in 1997 by the inventor in Abbenes, The Netherlands. 'Darwin's Pink Indulgence', was discovered growing amongst a large population of seedlings. The inventor grows over one million Delphiniums from seed each year for cut flower production and also evaluates and looks for plants that are unique and have market potential. The seeds that are sown are collected from open-pollinated plants and therefore the parentage is unknown. The parentage of the plants that were open-pollinated are also unknown as they were seedlings as well and not asexually propagated plants.

The new variety of Delphinium, 'Darwin's Pink Indulgence' is a unique cultivar. It is characterized by its compact habit and by its purple violet, fully double flowers that are long blooming. In addition, the flower stems of the new invention are desirable as a cut flower due to their ability to last 1.5 weeks after cutting, the presence of lateral branches, and a bloom color that does not darken with age.

'Darwin's Pink Indulgence' is unlike any existing cultivar of Delphinium. Double flowers exist on other cultivars, but flowers are typically defined as having 8 petals in place of the typical 4. 'Darwin's Pink Indulgence' has a combination of 22 petals and petaloids. No other Delphinium of this type known to the inventor or recorded in the literature has double flowers like 'Darwin's Pink Indulgence'.

There are other cultivars included in the Elatum Group of Delphiniums that are classified in the small to dwarf group (defined as reaching less than 1.5 m) that also have double flowers. None of these cultivars have double flowers to the extent of 'Darwin's Pink Indulgence' and none of them have a flower color that is similar to that of the new variety. The cultivar that is the closest in comparison is 'Eminence' (unpatented). Although it has double flowers and is similar in height, it differs from 'Darwin's Pink Indulgence' in that the flowers are double only to the extent as described above and they do not have the numerous petaloids that 'Darwin's Pink Indulgence' has. The flower color of 'Eminence' is a salmon pink (RHS 49D) rather than purple-violet like those of the new invention.

Asexual reproduction of the new cultivar was first accomplished by tissue culture in Abbenes, The Netherlands by the inventor in 1998. The liners were produced by tissue culture, planted in the field and the invention was subsequently propagated by cuttings. The characteristics of this cultivar have been determined to be stable and are reproduced true to type in successive generations both by vegetative cuttings and by tissue culture.

SUMMARY OF THE INVENTION

The following traits have been repeatedly observed and represent the characteristics of the new cultivar. These attributes in combination distinguish this cultivar from other commercial varieties. 'Darwin's Pink Indulgence' has not been tested under all possible conditions and phenotypic differences may be observed with variations in environmental, climatic, and cultural conditions:

1. 'Darwin's Pink Indulgence' has purple violet double flowers are unique: 5 showy sepals, 4 petals and 18 petaloids.
2. 'Darwin's Pink Indulgence' has a compact growth habit with a height of 90 cm and a spread of 40 cm.
3. The flower stems of 'Darwin's Pink Indulgence' are ideal for cuttings: lasting 1.5 weeks after cutting.
4. 'Darwin's Pink Indulgence' has a long bloom period: individual stems bloom for approximately 4 weeks with side branches blooming later for a total bloom period of approximately 12 weeks.

BRIEF DESCRIPTION OF THE DRAWINGS

The photograph on sheet one depicts shows the entire plant to clearly show the plant habit and the form of the flower stems.

The photograph on sheet two is a close-up of the flowers.

Sheet three contains a photograph of an adaxial view of both a leaf and an individual flower placed on a ruler in cms to show the length of the leaf and the diameter of the flower.

The photograph on sheet four provides the same information, however, an abaxial view of both the leaf and the individual flower is shown. The colors in these photographs are as accurate as possible by conventional photography. All photographs were taken of a plant grown outdoors in Abbenes, The Netherlands in a 2 gallon container.

BOTANICAL DESCRIPTION OF THE PLANT

The following is a detailed description of the new cultivar. The observed plant was 2 years old and was grown outdoors on open ground in Abbenes, The Netherlands. The color determination is in accordance with The R.H.S. Colour Chart of The Royal Horticultural Society, London, England, except where general color terms of ordinary dictionary significance are used.

Botanical classification: Delphinium 'Darwin's Pink Indulgence'. A Delphinium of hybrid origin belonging to the Elatum Group (also referred to as *Delphinium elatum* types) of which *Delphinium elatum* (unpatented) is considered to be a significant parent.

Common name: Larkspur.

Commercial classification: Hardy perennial for landscape use.

Parentage: Seedling selection of open-pollinated seedlings of hybrid Delphiniums.

Plant description:

*Blooming period.*—Late summer, total length of bloom is approximately 12 weeks.

*Plant habit.*—Upright, conical, clump-forming.

*Height and spread.*—90 cm in height and 40 cm in spread.

*Hardiness.*—Zone 4–8.

*Type.*—Hardy herbaceous perennial.

*Root system.*—Fibrous, but very fine root structure.

*Culture.*—Fertile, moisture retentive soils in full sun.

*Diseases and pests.*—No particular susceptibility or resistance observed.

Propagation:

*Methods of propagation.*—Basal cuttings, tissue culture.

*Time required to initiate new roots.*—Approximately 14 days at 14° C.

*Time required to develop roots.*—Approximately 35–40 days at 20° C. during the summer months to develop a fully developed rooted cutting in a 104 cell.

*Cropping time.*—Approximately 6 months from a rooted cutting to a flowering size plant in a 2 L. container.

Stem description:

*Shape.*—Round.

*Size.*—Average of 4 mm in diameter.

*Surface.*—Glabrous, the lower portion, near the base of main stem are covered with pale grey hairs, less than 0.5 mm in length.

*Color.*—138A.

*Branching.*—Basally from the roots, typically 2 lateral branches are observed on flowering stems.

*Internode length.*—3.5 cm (average).

Foliage description:

*Shape.*—Orbicular in outline but deeply lobed.

*Division.*—Palmately lobed to pedately lobed, typically 7 lobed, upper leaves are 3 lobed.

*Apex.*—Acute.

*Base.*—Cuneate.

*Venation.*—Palmate.

*Margins.*—Incised.

*Arrangement.*—Single leaves arranged alternately.

*Attachment.*—Petiolate.

*Surface.*—Dull (some gloss observed near the base), densely covered with short greyish-white hairs primarily on the lower surface and on the margins, upper surface is primarily glabrous.

*Size.*—21 cm in length and 30 cm in width (averages).

*Leaf color.*—Upper surface, young leaves: varies from 144Ato 143B. Lower foliage, young leaves: 143C. Upper foliage, mature leaves: varies from 137A to 137B. Lower foliage, mature leaves: varies from 138A to 191A. Vein color, upper surface: 137A. Vein color, lower surface: 191A.

*Petioles.*—8.0 cm in length (average), triangular in shape; 4 mm in height, 6 mm in width (averages), color 144A.

Flower description:

*Type.*—Terminal raceme of zygomorphic, double, rotate flowers.

*Fragrance.*—None.

*Size.*—6 cm in diameter, 2.3 cm in height excluding spur, 3 cm in height including the spur (averages).

*Quantity.*—25 per raceme, 90 per plant (averages).

*Orientation.*—Outward facing.

*Blooming characteristics.*—Flowers open from the base towards the apex over approximately a 4 week period. Individual flowers last approximately 2 weeks. Flowers are self-cleaning.

*Longevity as a cut flower.*—1.5 weeks.

*Peduncle.*—Held upright, up to 8 mm in diameter, 85 cm in length, color varies from 137A to 147A.

*Pedicels.*—Strong, held at a 30° angle, 6.5 cm in length, 2 mm in diameter, color varies from 137A to 147A.

*Bracts.*—2, linear shape, entire margins, apex is acuminate, opposite (sometimes alternate) arrangement, appearance is dull, texture is smooth, 1.5 cm in length, 0.8 mm in diameter, color is 146A with purplish tints.

*Bud.*—Oval to orbicular in shape, 1.1 cm in diameter, 3 cm in length including sepal spur, 1.8 cm in length excluding the spur, color is 77B–D (range).

*Sepals.*—Type: apopetalous, overlapping, posterior sepal is spurred, all petaloid. Number: 5. Size: Posterior sepal is 3.3 cm in length and 2.2 cm in width, other 4 sepals are 3.0 cm in length and 2.0 cm in width. Shape: Elliptic. Margins: Entire. Apex: Obtuse. Color: Upper side, when opening 81D–82D (range); Under side, when opening 78B–78C (range); Upper side, fully opened varies from 75B to 84B; Under side, fully opened varies from 75Ato84B; fading to 78D (both surfaces). Appearance: Dull. Texture: Glabrous.

*Petals and petaloids.*—Number: approximately 22 (4 petals and 18 petaloids from converted stamens). Size: 3.0 cm in length, 1.8 cm in width. Color: Immature 78C, mature 78C–D (range). Appearance: Dull. Arrangement: Rotate. Shape: Elliptic to obovate. Margins: Lobed towards the tip, less than ⅓ the petal length. Color; Immature 78C (both surfaces), Mature 78C to 78D (both surfaces).

*Reproductive organs.*—Stamens: Either converted to petaloids or abortive. Those abortive (approximately 10) are either anther-less or pollen-less anthers that are broadly club-shaped, 4 mm in length. Pistil: 5–6, pistil is 3 mm in length, stigma is whitish (not on chart), 2-parted to club-shaped, style is pale purple, 78C–D (Intermediate), in color. Fruit: Ovary is 145A in color, superior in position, becomes a dry dehiscent follicle, approximately 1.5 mm in diameter, color when dry is dark brown to almost black 202A.

I claim:

1. A new and distinct cultivar of Delphinium plant named 'Darwin's Pink Indulgence', as described and illustrated.

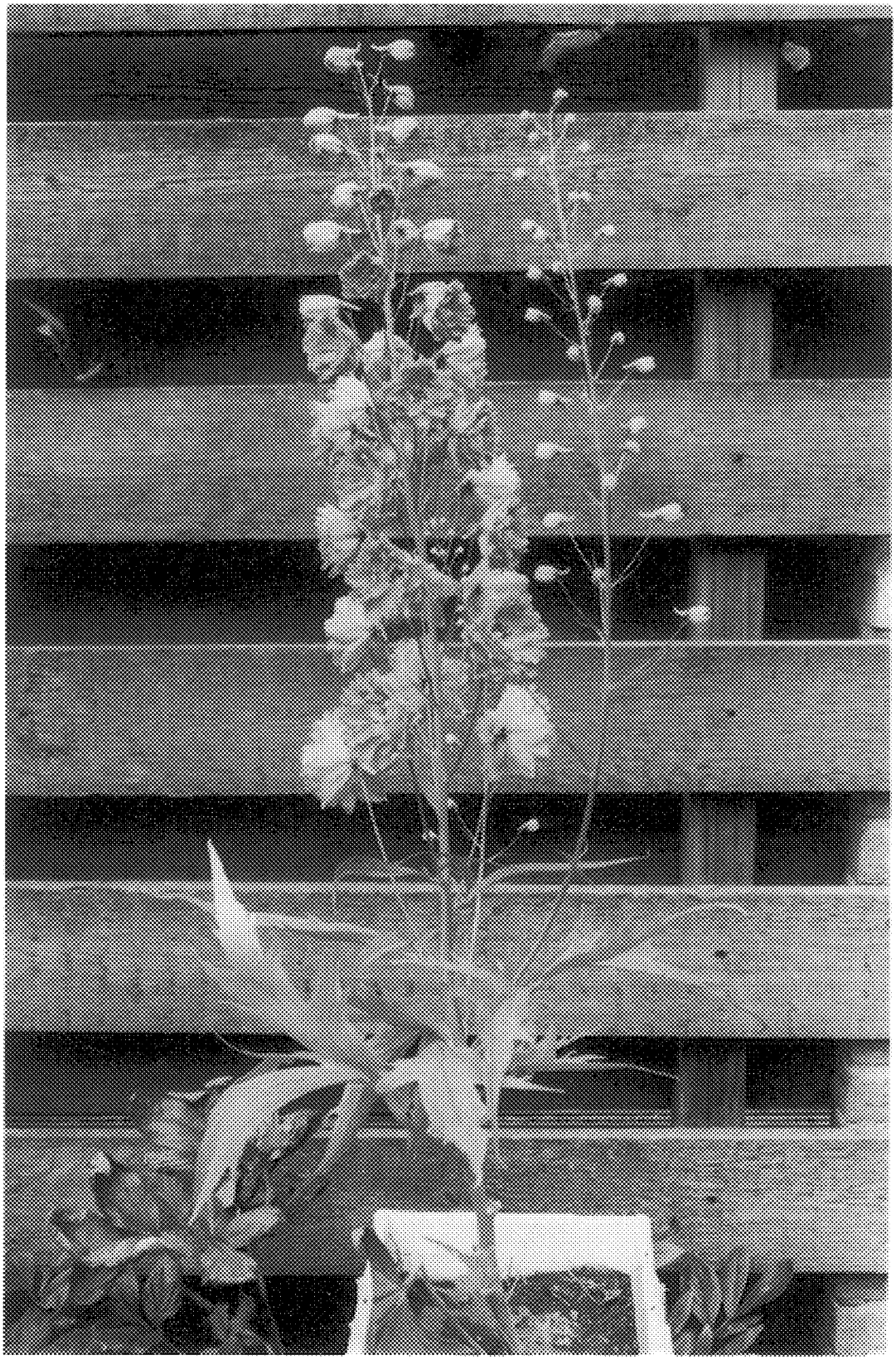

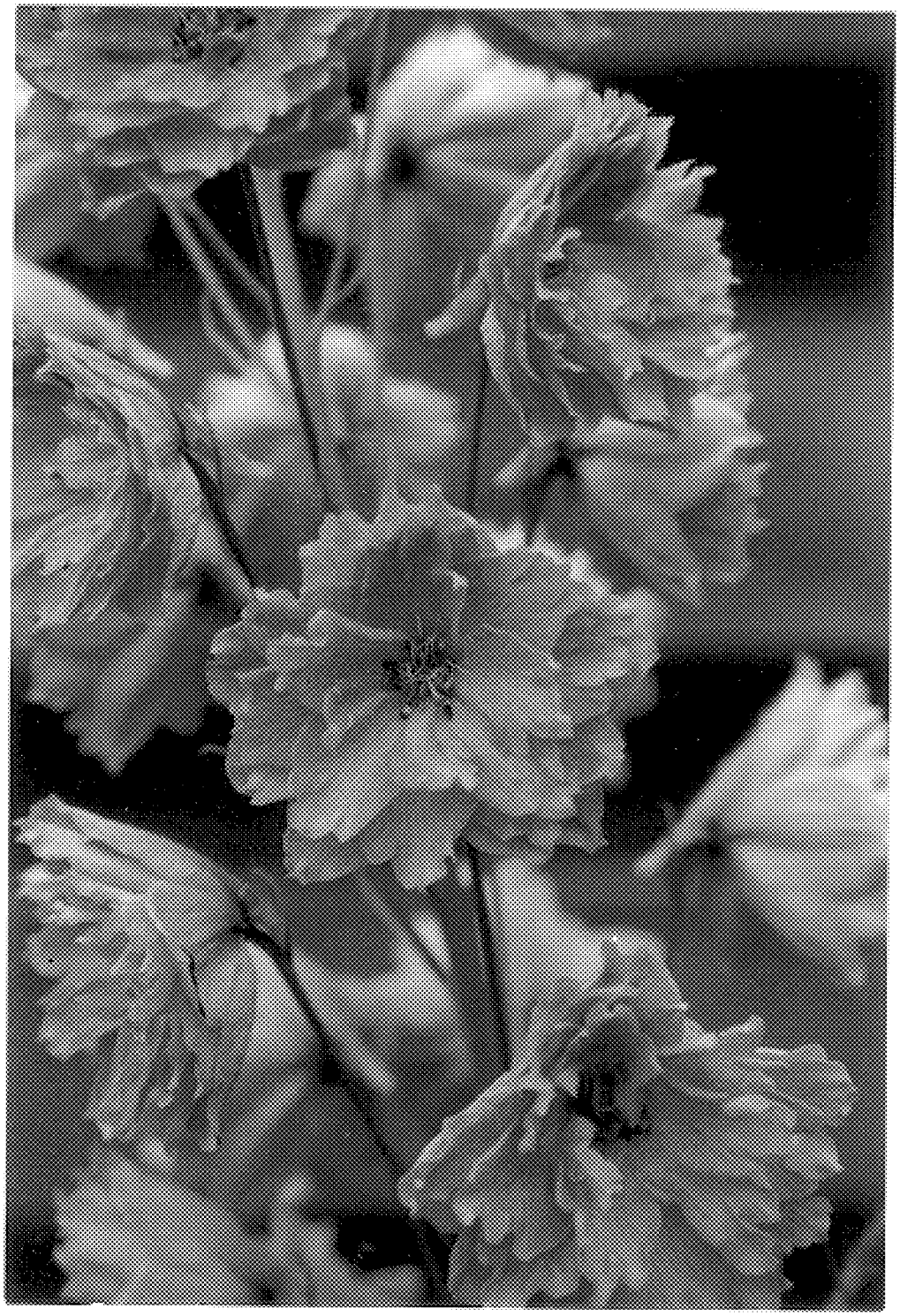

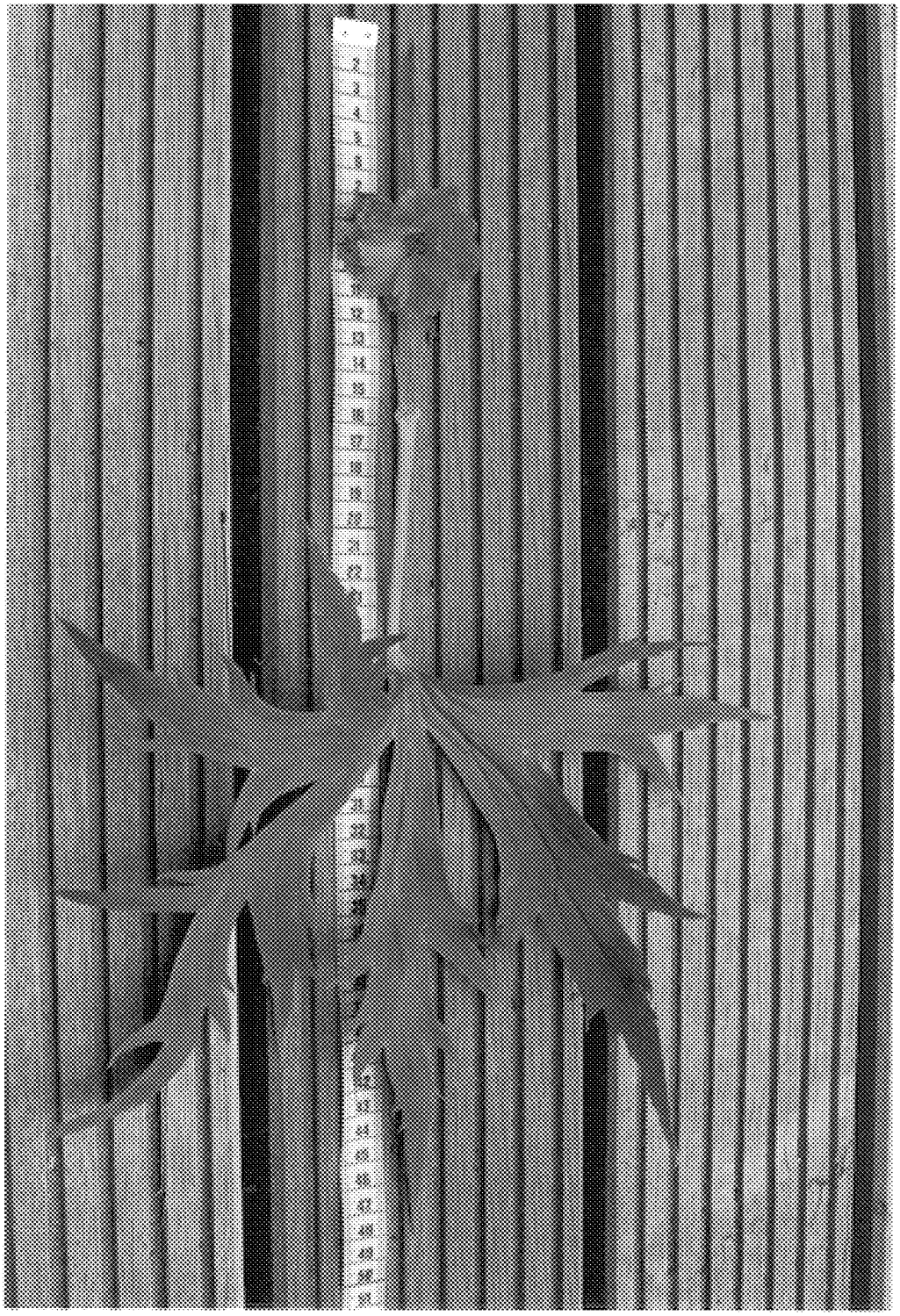

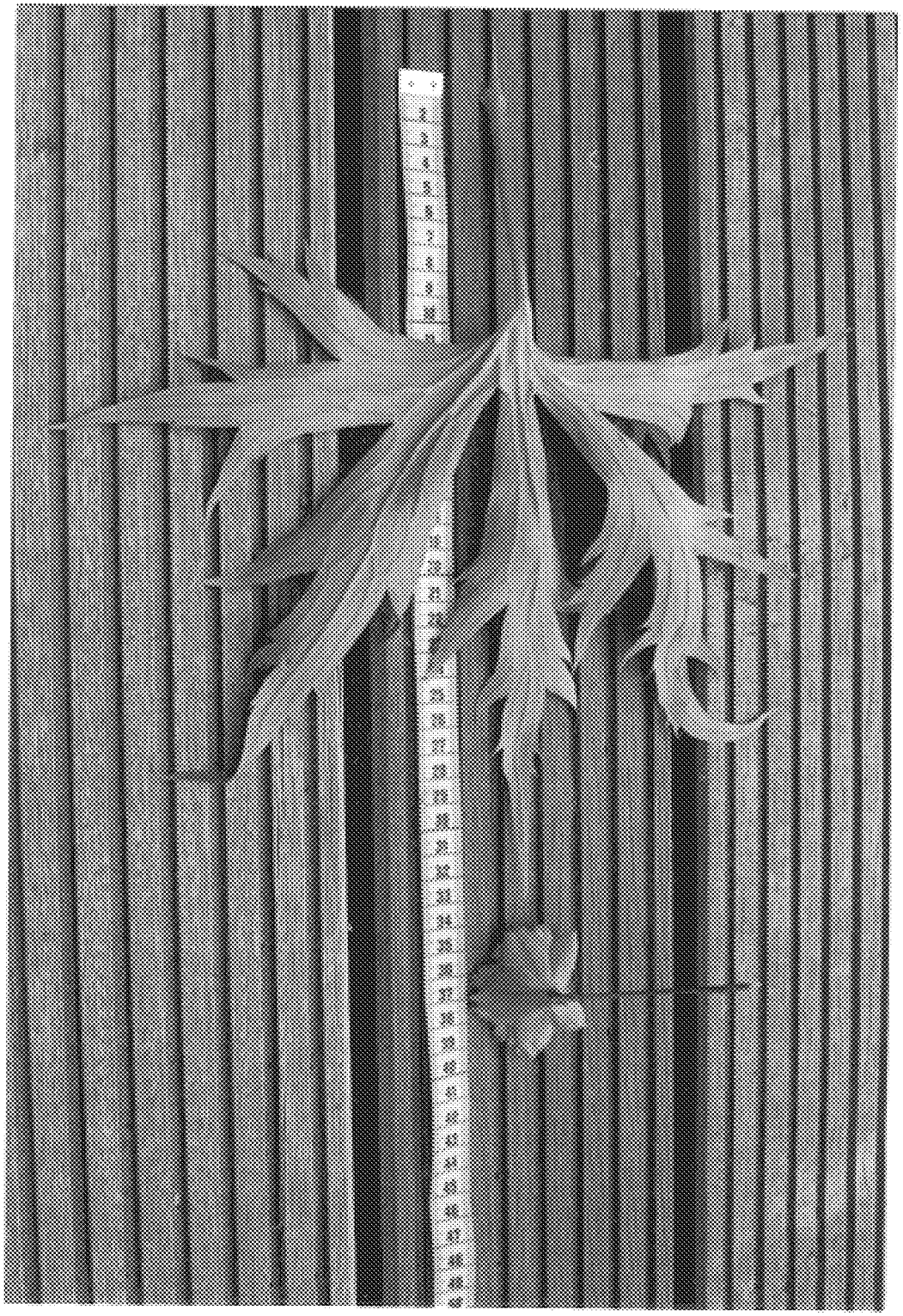

* * * * *